(12) United States Patent
Olivier

(10) Patent No.: US 10,314,500 B2
(45) Date of Patent: Jun. 11, 2019

(54) TRANSCUTANEOUS PHOTOPLETHYSMOGRAPHY

(71) Applicant: LifeQ Global Limited, Dublin (IE)

(72) Inventor: Laurence Richard Olivier, Alpharetta, GA (US)

(73) Assignee: LifeQ Global Limited, Dublin (IE)

(*) Notice: Subject to any disclaimer, the term of this patent is extended or adjusted under 35 U.S.C. 154(b) by 69 days.

(21) Appl. No.: 15/118,183

(22) PCT Filed: Feb. 10, 2015

(86) PCT No.: PCT/US2015/015137
§ 371 (c)(1),
(2) Date: Aug. 11, 2016

(87) PCT Pub. No.: WO2015/123175
PCT Pub. Date: Aug. 20, 2015

(65) Prior Publication Data
US 2017/0172433 A1    Jun. 22, 2017

Related U.S. Application Data

(60) Provisional application No. 61/940,020, filed on Feb. 14, 2014.

(51) Int. Cl.
| | |
|---|---|
| *A61B 5/00* | (2006.01) |
| *A61B 5/024* | (2006.01) |
| *A61B 5/0285* | (2006.01) |
| *A61B 5/08* | (2006.01) |
| *A61B 5/021* | (2006.01) |
| *A61B 5/02* | (2006.01) |

(Continued)

(52) U.S. Cl.
CPC ........ *A61B 5/02416* (2013.01); *A61B 5/0002* (2013.01); *A61B 5/0285* (2013.01); *A61B 5/02125* (2013.01); *A61B 5/0816* (2013.01); *A61B 5/02* (2013.01); *A61B 5/0295* (2013.01); *A61B 5/02116* (2013.01); *A61B 5/02427* (2013.01); *A61B 5/14552* (2013.01); *A61B 5/6813* (2013.01); *A61B 5/7235* (2013.01)

(58) Field of Classification Search
CPC ..... A61B 5/0002; A61B 5/02; A61B 5/02116; A61B 5/02125; A61B 5/02416; A61B 5/02427; A61B 5/0295; A61B 5/14552; A61B 5/6813; A61B 5/7235; A61B 5/0285; A61B 5/0816
See application file for complete search history.

(56) References Cited

U.S. PATENT DOCUMENTS

| | | |
|---|---|---|
| 2010/0305418 A1 | 12/2010 | Deliwala |
| 2011/0224499 A1 | 9/2011 | Banet et al. |

(Continued)

FOREIGN PATENT DOCUMENTS

| | | |
|---|---|---|
| WO | WO 2009/125349 | 10/2009 |

*Primary Examiner* — George Manuel
(74) *Attorney, Agent, or Firm* — Smith Gambrell & Russell LLP; Gregory Kirsch; Matthew Warenzak

(57) ABSTRACT

The present invention discloses a reflectance type PPG-based physiological sensing system with a close proximity triangulation approach toward robustly measuring several physiological parameters including, but is not limited to, heart rate, breathing rate, blood oxygen saturation and pulse wave velocity.

23 Claims, 5 Drawing Sheets

(51) Int. Cl.
*A61B 5/0295* (2006.01)
*A61B 5/1455* (2006.01)

(56) References Cited

U.S. PATENT DOCUMENTS

2013/0046192 A1  2/2013  Lin et al.
2014/0121494 A1* 5/2014  Adler, Jr. ............. A61B 5/4836
                                             600/411

* cited by examiner

TRANSCUTANEOUS PHOTOPLETHYSMOGRAPHY

FIELD OF THE INVENTION

The present invention pertains mainly to physiological/vital sign monitoring by making use of close-proximity triangulation photoplethysmography—in particular by enabling robust and accurate determination of physiological parameters, including but not limited to heart rate, breathing rate and pulse wave velocity.

BACKGROUND OF THE INVENTION

Traditionally, health monitor devices were only applicable in fixed hospital/medical settings, using expensive, high tech machinery relying on trained medical personal. Recently however, portable health monitoring devices have become a growing trend in modern healthcare to provide continuous physiological information to the wearer and/or to guide healthcare practitioners in their medical decisions. Continuous access to physiological parameters can be widely beneficial in a scientific and clinical research setting, as well as in the sport and fitness sector to motivate and guide users to achieve and maintain personal health, wellness and fitness goals.

Photoplethysmography (PPG) is a well-known optical sensing technique used to measure the hemodynamic properties in organisms. Transcutaneous PPG technology essentially entails the illumination of the skin of an organism and the subsequent photo-detection of reflected or transmitted light through a sample in order to measure small changes in light intensity. These small changes in light intensity are due to shifts in the concentration of several subcutaneous chromophores (molecules that absorb light). These concentration changes occur due to changes in subcutaneous blood volume due to the level of tissue perfusion as a result of (i) expansion and contraction of capillary vessels during the cardiac cycle and (ii) subcutaneous fluid movement due to motion of the organism. Several transformations of the PPG signal have been proposed and implemented to obtain physiological parameters from the PPG signal, and several algorithms and embodiments have been proposed to yield accurate, motion resistant physiological parameters, such as heart rate and oxygen saturation, from wearable PPG sensors.

Progress has been made to reduce the cost of wearable PPG-based sensors that are resistant to motion artifacts, but most of the PPG solutions currently employed use a combination of optical and accelerometer based solutions to accurately determine heart rate. US Patent Application Publication 20140213863 to Texas Instruments Inc. describes a PPG-based heart rate monitor is that uses an optical motion sensor to remove artifacts. A reference signal for motion compensation is generated either by a incorporating a second light emitting diode (LED) of a different wavelength, alternatively, by either lowering the driving current of the primary LED or by changing the wavelength of the primary LED, which is subtracted from the desired heart rate signal to correct for motion artifacts. In U.S. Pat. No. 8,483,788 to Covidien Lp. a motion compensated pulse oximeter is described that includes an accelerometer to measure the changes induced by motion between the LED and the photodetector. Furthermore, US 20140058217 described a pulse PPG device including motion artifact mitigation methods. Here, a first circuit comprises a PPG-based sensor, while a second circuit comprised of an impedance-based sensor for surface motion artifacts. Currently, PPG technologies are still inherently susceptible to motion artifacts, therefore, they are limited to measure heart rate and oxygen saturation as there is no PPG based device that resolves this problem satisfactory during severe bouts of physical activity.

Furthermore, currently no device, applied to a single point (defined as a surface not larger than a circle with 1.5 inch radius) on the body, can accurately gauge the velocity of a heart beat pulse propagated through the arterial circulation. This phenomenon is known as pulse wave velocity and there exist several optical based solutions where optical sensing modules are placed on different sites of the organism. For example, U.S. Pat. No. 7,674,231 B2 describes a wearable pulse wave velocity blood pressure sensor to perform circulatory measurements on an extremity of a subject. Here, a first PPG signal is obtained from a first position on the subject (such as the wrist) and a second PPG signal at a second position on the extremity (such as a digit). Alternatively, combination approaches exist where an optical sensing module and ECG are employed. For example, in U.S. Pat. No. 6,331,162 B2 claims to analyze blood flow by recording PPG-based waveforms at two locations along the descending thoracic aorta, while simultaneously recording the ECG waveform of the subject in order to determine pulse wave velocity.

SUMMARY OF THE INVENTION

In one embodiment, the current invention overcomes many problems and disadvantages associated with reflectance type PPG-based physiological sensing by introducing close-proximity triangulation PPG.

Close-proximity triangulation PPG entails the simultaneous PPG measurement at three, or more, independent sites that are in close proximity. In a preferred embodiment the measurement sites are spaced apart to form an equilateral triangle within a single point (as defined previously as a surface not larger than a circle with 1.5 inch radius). The respective PPG measurements are subsequently digitized and used to accurately determine physiological metrics by feeding the respective PPG measurements to an on-board processor and/or for processing on a secondary device/server, where said processing includes DSP algorithms such as dynamic time warping.

Close-proximity triangulation PPG is used towards identifying and removing motion artifacts from optical signals obtained from a wearable optical sensor device that acquired optical signals during extreme bouts of physical activity and movement. In addition, the current invention makes use of close-proximity optical sensing triangulation which enables one to determine the direction and velocity of the blood pulse wave, thus enabling one to gauge arterial stiffness and estimate blood pressure. Pulse wave velocity is a reliable prognostic parameter for cardiovascular morbidity and mortality that can be used in a variety of adult populations including patients with diabetes, hypertension and end-stage renal disease.

Furthermore, the pulse wave velocity data can be used to aid in the separation of motion artifacts and physiological features such as heart rate. The different wave propagation characteristics for physiological features and motion artifacts, as determined by triangulation PPG is used to decompose motion and physiological features.

While the present invention is described in detail with reference to various embodiments in subsequent pages, it will be appreciated that the present invention is not limited to the embodiments described herein, and that modifications may be made without departing from the scope of the invention defined in the accompanying description.

In one embodiment the present invention discloses a reflectance type PPG-based physiological sensing system with a close-proximity triangulation sampling approach (from here on called close-proximity triangulation PPG or tPPG) towards robustly measuring several physiological parameters and compensating for motion artifacts. The measured physiological parameters include, but not limited to, heart rate, breathing rate, oxygen saturation and pulse wave velocity.

The tPPG-based physiological sensing system comprises a wearable optical sensing module (contained in a wearable device). The optical sensing module contains three or more light-emitting diodes and three or more light-sensitive components (such as a phototransistor or photodiode) arranged, in a preferred embodiment, in a triangular fashion. The optical sensing module measures blood volume changes caused by the expansion and contraction of the blood capillaries in the skin and underlying tissue during the cardiac cycle (and other processes such as Mayer waves).

The design of the optical sensing module enables rapid simultaneous or rapid sequential sampling at the respective measuring sites. The measurements at the respective spatial points allows for the mathematical determination of physiological parameters such as the pulse wave vector. These measurements, apart from having clinical value, can also be used to effectively compensate for motion artifacts that occurs during measurement of physiological metrics such as, but not limited to, heart rate, breathing rate & oxygen saturation.

BRIEF DESCRIPTION OF DRAWINGS

The accompanying figures, where alike reference numerals refer to identical or functionally similar elements throughout the separate views, and which together with the detailed description below are incorporated in and form part of the specification, serve to further illustrate various embodiments of, and to explain principles in accordance with, the present invention.

The present invention is described by way of an exemplary embodiment with reference to the accompanying representations, not drawn to any scale, in which:

FIG. 2A illustrates a measurement island (2) consisting of a light detector (1) and two light sources (3) (able to transmit similar or different wavelengths) on either side of the light detector.

FIG. 2B illustrates a measurement island (2) consisting of a light detector (1) and one light source (3) next to the light detector (1).

FIG. 2C illustrates a measurement island (2) consisting of a light detector (1) and one monolithic light source (5) next to the light detector (1).

DETAILED DESCRIPTION OF THE PREFERRED EMBODIMENTS

The following detailed description and appended drawings describe and illustrate various aspects of the present invention. The descriptions, embodiments and figures are not intended to limit the scope of the invention in any way.

Figure 1:
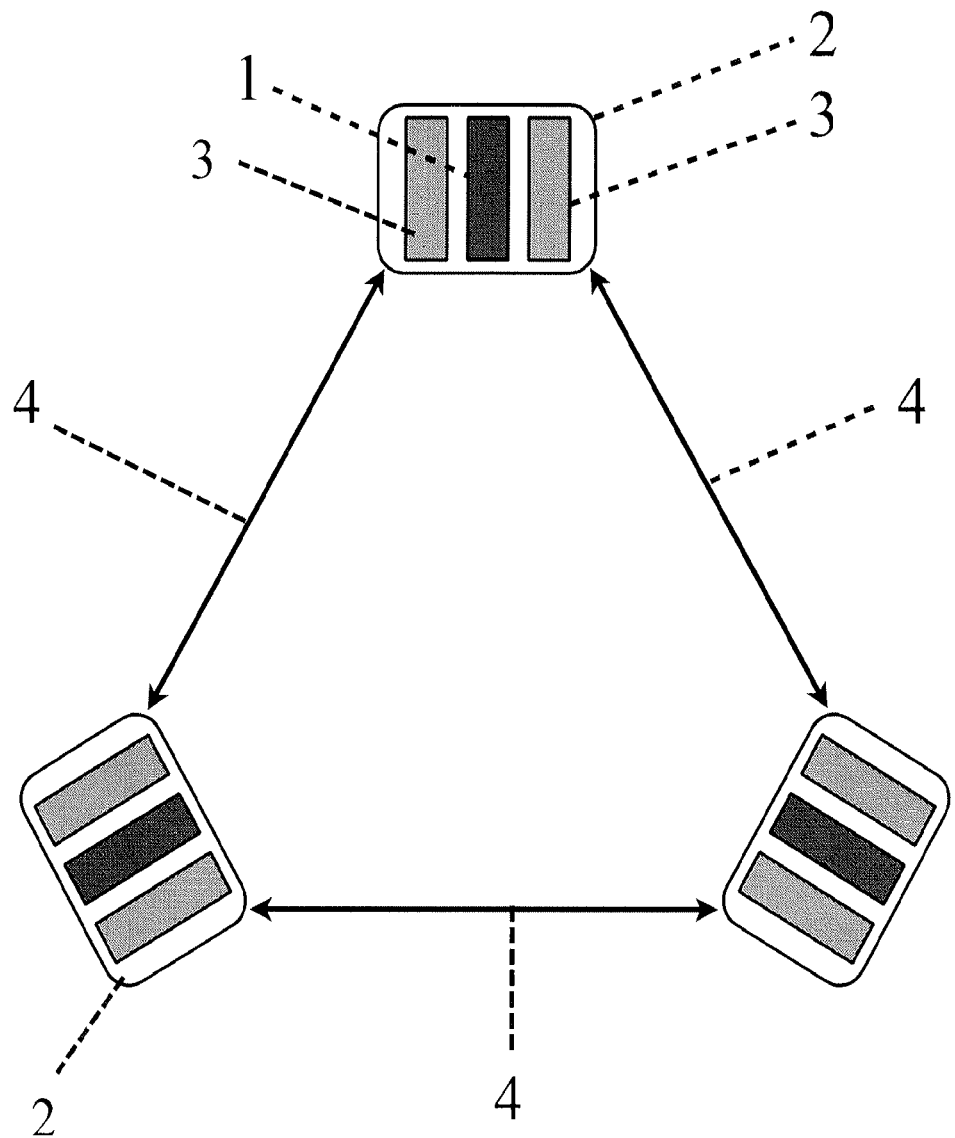
FIG. 1 is a conceptual illustration of the exemplary embodiment of the tPPG-based physiological sensing system comprising three measurement islands (2) (with each island consisting of a light detector (1) and two light sources (3) on either side of the light detector (1)) arranged to form the nodes of an equilateral triangle of a given size (4).

FIG. 1 is a conceptual illustration of the exemplary embodiment of the tPPG-based physiological sensing system comprising three measurement islands (2) (with each island consisting of a light detector (1) and two light sources (3) on either side of the light detector) arranged to form the nodes of an equilateral triangle. The distance (4) between measurement islands (2) is as such that the light sources (3) of the respective measurement islands do not interfere with the light detectors (1) of the respective measurement islands (2). There might however still exist minor light contaminations between the respective sensing islands that can be compensated for analytically/mathematically. The respective measurement islands (2) are used to measure the blood pulse wave characteristics such as velocity and direction of the wave by analyzing the timing of the PPG peaks and PPG characteristics between the respective measurement islands. The PPG peak time at the three measurement islands can, for instance, be used to calculate the speed of wave propagation, as the distance (4) between the measurement islands (2) is known.

Figure 2:
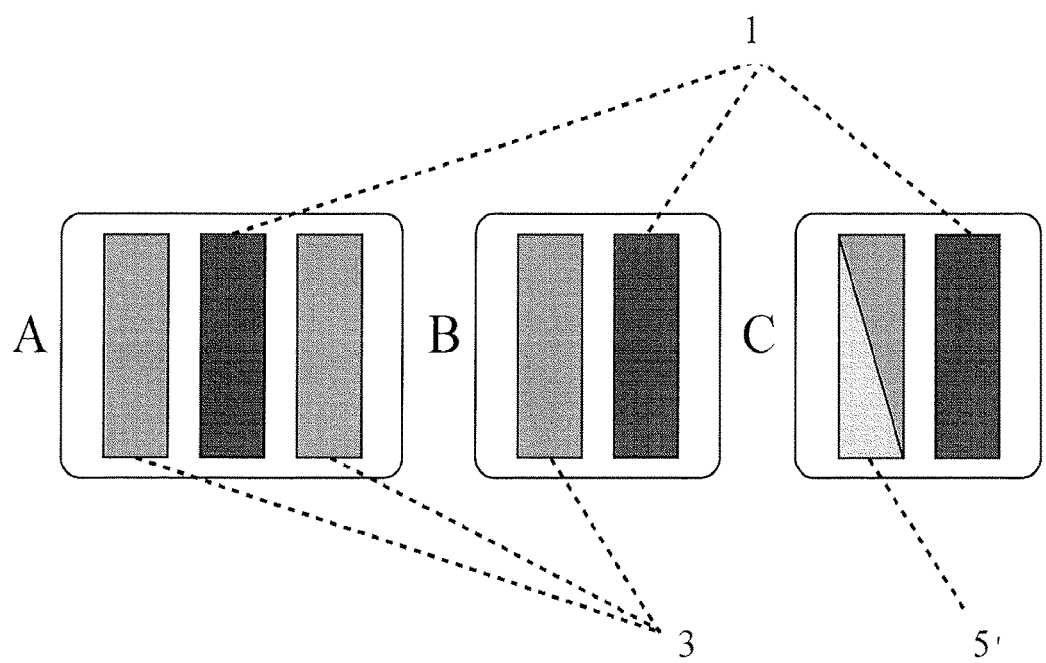
FIG. 2 is a conceptual illustration of some of the types of measurement islands (2).

FIG. 2 is a conceptual illustration of some of the types of measurement islands (2). While many different measurement island configurations are possible, three of the types of measurement islands are briefly discussed.

FIG. 2A illustrates a measurement island (2) consisting of a light detector (1) and two light sources (3) (able to transmit similar or different wavelengths) on either side of the light detector. In the case where the two light sources (3) are of the same wavelength, the two light sources are programmed to simultaneously emit light, and the light detector (1) such as a photodiode or phototransistor then subsequently detects the reflected light coming back from the skin. However, in the case where the two light sources (3) are of different wavelengths, the two light sources are programmed to sequentially emit light, and the light detector (1) then subsequently detects the reflected light.

FIG. 2B is the simplest measurement island configuration where a single light source (3) transmits a specific wavelength into the skin and the light detector (1) measures the reflected light.

FIG. 2C illustrates a similar methodology and configuration as in FIG. 2A, but in this case two different wavelengths are encapsulated into a single monolithic light source (5).

Figure 3:
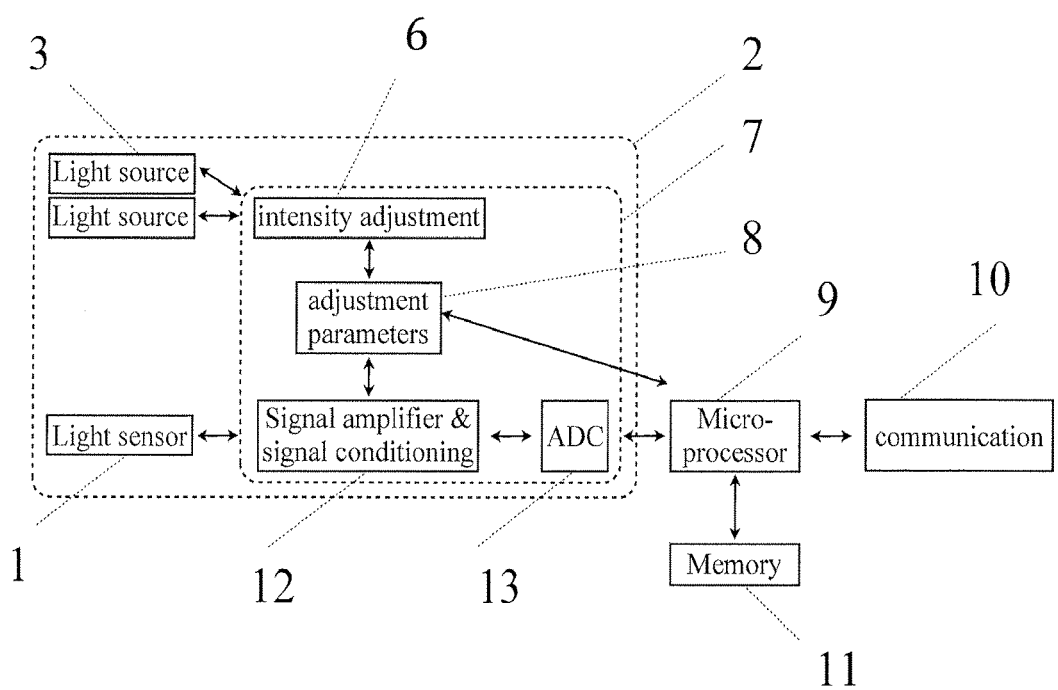
FIG. 3 is a conceptual illustration of the interaction of the electronic components of a single optical measurement island (2) and peripheral electronics.

FIG. 3 conceptually illustrates the electronic components involved for a single measurement island (2) with peripheral electronics included. A microprocessor (9) instructs a signal module (7) by adjusting several adjustment parameters (8) (containing parameters for intensity adjustment (6) and signal amplification & signal conditioning (12)) that affects the light source (3) intensity as well as the signal amplification and conditioning measured by the light sensor/detector (1). The amplified and conditioned signal is then digitized by an analog to digital converter (ADC) (13). Subsequently the digitized values are pushed to a microprocessor (9) to store the digitized signals on memory (11) and/or communicate it to peripheral electronics by a communication module (10). The communication module can either be wired or wireless. In addition, digitized signal values obtained by the microprocessor can be used to readjust the adjustment parameters (8) in order to obtain a signal with maximum resolution and the least amount of noise.

Figure 4:
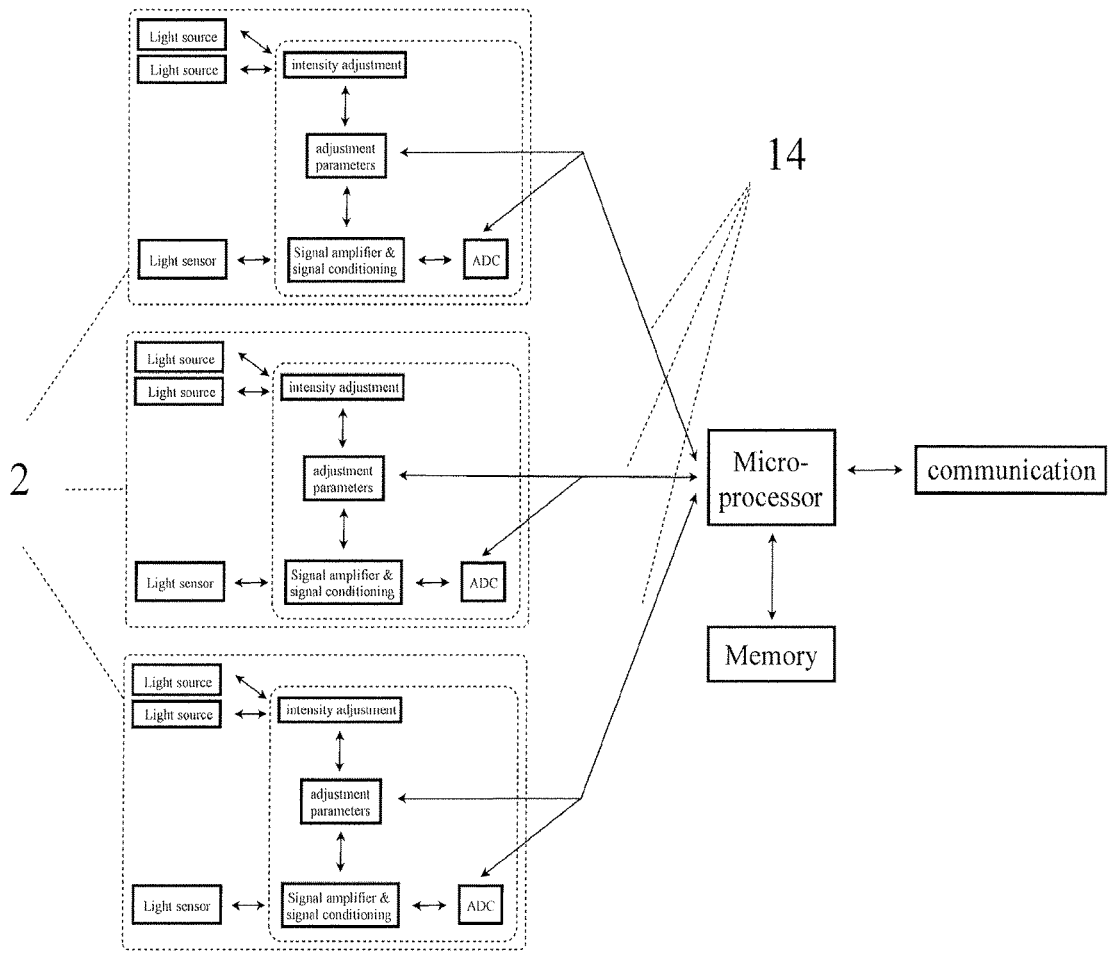
FIG. 4 is a conceptual illustration of the electronic components comprising the preferred embodiment of the complete optical sensing module.

FIG. 4 depicts the same configuration as in FIG. 3, but shows that multiple measurement islands (2) can be coupled (14) to a single microprocessor, storage and communication module. In this case the preferred embodiment is displayed with three islands present.

Figure 5:
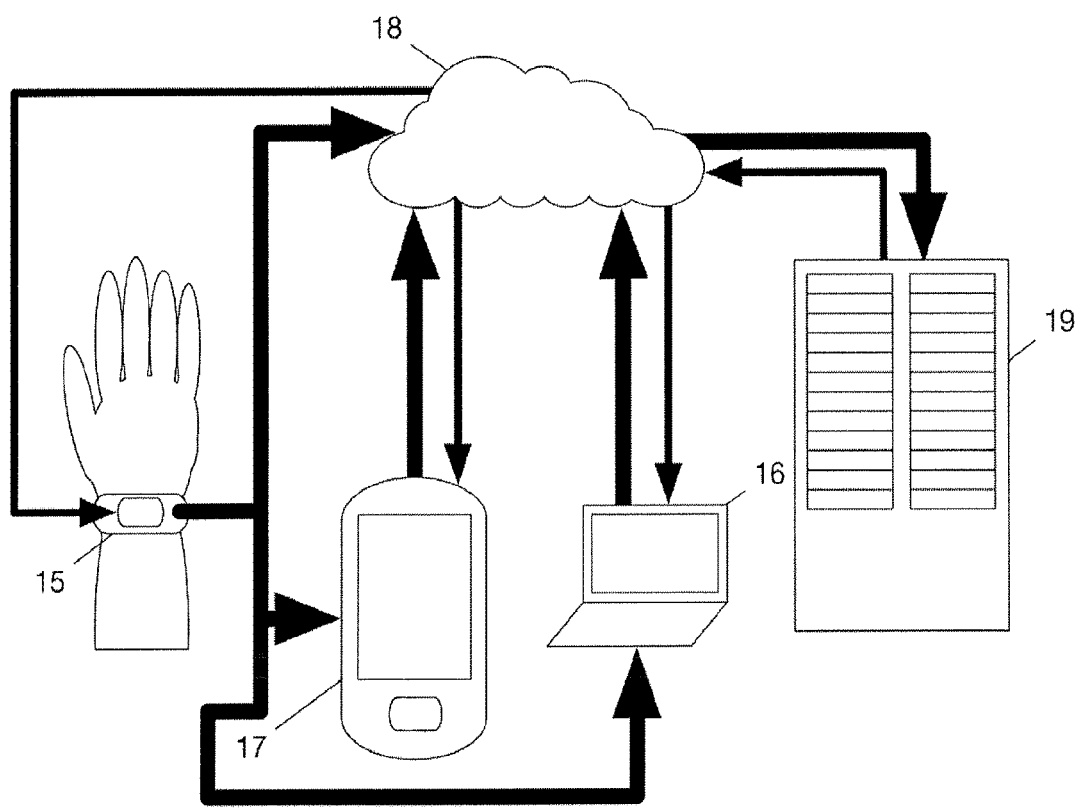
FIG. 5 illustrates a basic embodiment of the invention in the context of mobile and internet technologies.

FIG. 5 is a schematic illustration of a wearable device (15) for obtaining physiological parameters of a subject, which in this embodiment may be a human, but could also be an animal or other organism or process. The physiological sensors are incorporated into a band, which contacts the skin and may be worn on parts of the body including, but not limited to, the wrist, forearm and upper arm. The device optionally contains a display unit and is capable of transmitting data to a mobile device, such as a personal computer (16), mobile phone (17) and/or the Internet. The data may be stored (18) and further processed on a server (19) for future use and can be viewed on a computer platform such as a personal computer, mobile phone and/or a wearable device.

What is claimed:

1. A method for the determination of at least one physiological parameter by way of close proximety triangulation photoplethysmography (PPG) comprising;
   (a) measuring a PPG signal at different sensor measurement islands within a single point on a subject, wherein the different sensor measurement islands comprise at least three sensor measurement islands located from one another at known distances;
   (b) measuring pulse wave characteristics of the PPG signal, wherein the pulse wave characteristics comprise velocity, direction and magnification of wave phenomena;
   (c) measuring the timing of PPG peaks and PPG characteristics of the PPG signal between sensor measurement islands;
   (d) amplifying and conditioning the PPG signal;
   (e) converting amplified and conditioned signal(s) to a digital signal;
   (f) employing an algorithm to distinguish between biological waveforms derived from the PPG signal and to store the digital signal; and
   (g) transmitting the digitial signal and/or physiological parameters derived from said digital signal.

2. The method of claim 1, further comprising identifying common features and/or aligning raw features of the PPG signals from different sensor measurement islands to analyze the speed of the biological waveforms.

3. The method of claim 1, further comprising performing motion compensation and decomposition of the wave phenomena.

4. The method of claim 1, wherein the wave phenomena comprise pulse waves, Mayer waves, and motion artifacts.

5. The method of claim 1, further configured to determine a number of physiological parameters comprising heart rate, heart rate variability, respiration rate, blood oxygen saturation and/or pulse wave velocity.

6. The method of claim 1, wherein the measuring of the PPG signals at the different sensor measurement islands involves simultaneous and/or sequential PPG measurements.

7. The method of claim 1, wherein the distances between and illumination level of the different measurement islands prevents interference with light detectors of the different individual measurement islands.

8. The method of claim 1, further comprising adjusting and/or controlling adjustment parameters, wherein the adjusting and/or controlling comprises at least one of:
   adjusting light source intensity of at least one of the different individual sensor measurement islands;
   adjusting signal amplification and/or signal conditioning parameters; and
   readjusting said signal amplitude and signal conditioning parameters using obtained digitized signal values.

9. The method of claim 1, wherein the amplified and/or conditioned digital signal and/or physiological parameters derived from said digital signal is stored on memory and/or communicated to a mobile electronics device by a communication module.

10. The method of claim 1, wherein the transmitting the digitial signal and/or physiological parameters further comprises transmitting the digital signal and/or physiological parameters derived from said digital signal wirelessly to a platform where said data can be stored or processed on a server, analyzed and viewed on client computing platforms, including, but not limited to, mobile computing devices, home computers and/or a wearable device.

11. A wearable device configured to be worn against a user's skin and to determine at least one physiological parameter by way of close proximity triangulation photoplethysmography (PPG) of the user, the wearable device comprising;
   (a) at least three individual sensor measurement islands at a given spatial arrangement which are comprised of a plurality of optical sensing modules and electronic embodiment(s), wherein the at least three individual sensor measurement islands are configured for measuring a PPG signal, including measuring pulse wave characteristics of the PPG signal through the optical sensing modules, wherein the pulse wave characteristics comprise at least one of a velocity, direction, and magnification of wave phenomena;
   (b) a signal module configured to amplify and condition the PPG signal;
   (c) an analog to digital converter (ADC) to convert amplified and conditioned signal(s) to a digital signal;
   (d) a processor configured to measure the timing of PPG peaks and PPG characteristics between individual sensor measurement islands, distinguish between biological waveforms derived from the PPG signal, and store the digital signal; and
   (e) a transmitter to transmit the digitial signal and/or physiological parameters derived from said digital signal.

12. The wearable device of claim 11, wherein the at least three individual sensor measurement islands are spatially arrange in a configuration including, but not limited to, a triangular formation.

13. The wearable device of claim 11, wherein said optical sensing module(s) comprise one or more light-emitting diodes(s) and one or more light-sensitive components.

14. The wearable device of claim 11, where at least one of the at least three individual sensor measurement islands comprises:
   a plurality of the light source of different wavelengths programmed to sequentially emit light; and
   at least one light detector to subsequently detect the reflected light from the plurality of light sources.

15. The wearable device of claim 11, wherein at least one of the at least three individual sensor measurement islands comprises:
   a plurality of the light source(s) of the same wavelength programmed to simultaneously emit light; and
   at least one light detector to subsequently detect the reflected light from the plurality of light sources.

16. The wearable device of claim 11, wherein the processor is used in conjunction with at least three optical sensing modules to algorithmically separate and determine the speed, direction and magnitude of different biological waves, given the spatial arrangement of the at least three individual sensor measurement islands.

17. The wearable device of claim 11, wherein the wearable device is further configured to perform motion compensation and decomposition of the waveforms for measurement of physiological parameters, wherein the waveforms include pulse waves, Mayer waves, and motion artifacts.

18. The wearable device of claim 11 is further configured to determine a number of physiological parameters including, but not limited to, heart rate, heart rate variability, respiration rate, blood oxygen saturation and pulse wave velocity.

19. The wearable device of claim 11, wherein close-proximity triangulation PPG involves simultaneous and/or sequential PPG measurements at the at least three individual sensor measurement islands.

20. The wearable device of claim 11, wherein the individual distance and individual illumination level of each of the individual sensor measurement islands prevents interference with light detectors of the other plurality of individual sensor measurement islands.

21. The wearable device of claim 11, wherein the wearable device is further configured to:
   adjust light source intensity of at least one of the at least three individual sensor measurement islands;
   adjust signal amplification and/or signal conditioning parameters; and
   readjust said signal amplitude and signal conditioning parameters using obtained digitized signal values.

22. The wearable device of claim 11, further comprising memory and a communication module, wherein the amplified and/or conditioned digital signal and/or physiological parameters derived from said digital signal is stored on the memory and/or communicated to a mobile electronics device, such as a mobile phone or personal computer, by the communication module.

23. The wearable device of claim 11, wherein the transmitter is configured to transmit conditioned digital signal and/or physiological parameters derived from said digital signal wirelessly to a platform where said data can be stored or processed on a server, analyzed and viewed on client computing platforms, including, but not limited to, mobile computing devices, home computers and/or a wearable device.

* * * * *